US009220919B2

(12) United States Patent
Masumoto et al.

(10) Patent No.: US 9,220,919 B2
(45) Date of Patent: Dec. 29, 2015

(54) RADIOTHERAPY APPARATUS CONTROLLER AND RADIOTHERAPY APPARATUS CONTROL METHOD

(75) Inventors: Masanori Masumoto, Tokyo (JP); Hiroyuki Shibata, Tokyo (JP); Shuji Kaneko, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 308 days.

(21) Appl. No.: 13/816,021

(22) PCT Filed: May 24, 2011

(86) PCT No.: PCT/JP2011/061853

§ 371 (c)(1), (2), (4) Date: Feb. 8, 2013

(87) PCT Pub. No.: WO2012/042969

PCT Pub. Date: Apr. 5, 2012

(65) Prior Publication Data

US 2013/0178690 A1 Jul. 11, 2013

(30) Foreign Application Priority Data

Sep. 28, 2010 (JP) ................................ 2010-217356

(51) Int. Cl.
*A61N 5/00* (2006.01)
*A61N 5/10* (2006.01)

(52) U.S. Cl.
CPC ............ *A61N 5/1037* (2013.01); *A61N 5/1049* (2013.01); *A61N 5/1069* (2013.01); *A61N 2005/1061* (2013.01)

(58) Field of Classification Search
CPC .................... A61N 5/1037; A61N 2005/1061; A61N 5/1069; A61N 5/1049
USPC .................................. 600/1–3; 128/897–899
See application file for complete search history.

(56) References Cited

U.S. PATENT DOCUMENTS 6,516,046 B1 2/2003 Frohlich et al.
6,670,618 B1 12/2003 Hartmann et al.

(Continued)

FOREIGN PATENT DOCUMENTS

| CN | 101032650 | 9/2007 |
|---|---|---|
| DE | 199 07 065 | 8/2000 |

(Continued)

OTHER PUBLICATIONS

International Preliminary Report on Patentability and Written Opinion of the International Searching Authority issued Apr. 16, 2013 in International (PCT) Application No. PCT/JP2011/061853.

(Continued)

*Primary Examiner* — Navin Natnithithadha
*Assistant Examiner* — Sunita Reddy
(74) *Attorney, Agent, or Firm* — Wenderoth, Lind & Ponack, L.L.P.

(57) ABSTRACT

A radiotherapy apparatus control method includes: collecting a planning-stage position where a patient is arranged during a planning stage; collecting a position-adjusting-stage position where the patient is arranged during a position-adjusting stage; calculating a treatment-stage position, a gantry-angle offset value and a ring-angle offset value such that an orientation in which an irradiation head is arranged with respect to the treatment-stage position, when a ring is arranged while deviating from a ring angle by the ring-angle offset value and a gantry is arranged while deviating from a gantry angle by the gantry-angle offset value, coincides with an orientation in which the irradiation head is arranged with respect to the planning-stage position, when the ring is arranged at the ring angle and the gantry is arranged at the gantry angle. After that, the patient is arranged at a patient position.

18 Claims, 7 Drawing Sheets

10
RADIOTHERAPY APPARATUS CONTROLLER
TREATMENT PLAN COLLECTING SECTION — 61
PLANNING-STAGE POSITION DATA COLLECTING SECTION — 62
POSITION-ADJUSTING-STAGE POSITION DATA COLLECTING SECTION — 63
CORRECTION AMOUNT CALCULATING SECTION — 64
COUCH DRIVING SECTION — 65
IRRADIATION HEAD DRIVING SECTION — 66
IRRADIATING SECTION — 67

(56) References Cited

U.S. PATENT DOCUMENTS

| | | | | |
|---|---|---|---|---|
| 7,373,676 | B2 | 5/2008 | Markovic et al. | |
| 2005/0049478 | A1* | 3/2005 | Kuduvalli et al. | 600/407 |
| 2006/0072699 | A1 | 4/2006 | Mackie et al. | |
| 2006/0215813 | A1 | 9/2006 | Scherch et al. | |
| 2007/0211856 | A1 | 9/2007 | Urano et al. | |
| 2010/0056908 | A1* | 3/2010 | Giller et al. | 600/426 |
| 2010/0202588 | A1 | 8/2010 | Shibuya et al. | |

FOREIGN PATENT DOCUMENTS

| | | |
|---|---|---|
| DE | 199 53 177 | 6/2001 |
| EP | 1 832 312 | 9/2007 |
| JP | 2006-051215 | 2/2006 |
| JP | 2007-061482 | 3/2007 |
| JP | 2010-057810 | 3/2010 |
| JP | 2010-131270 | 6/2010 |
| JP | 2010-183976 | 8/2010 |
| WO | 2007/029520 | 3/2007 |

OTHER PUBLICATIONS

Extended European Search Report issued May 9, 2014 in corresponding European Patent Application No. 11828531.1.

International Search Report issued Jul. 19, 2011 in International (PCT) Application No. PCT/JP2011/061853.

Chinese Search Report issued Jan. 4, 2015 in corresponding Chinese Application No. 201180039350.3 (with English translation).

Decision to Grant a Patent issued Sep. 22, 2015 in corresponding Chinese patent application No. 201180039350.3.

* cited by examiner 34
48-2
43
51
42
41
49
52
45
46
53
47
44
48-1

34
48-2
51
42
41
52
53
46
47
45
44
48-1

RADIOTHERAPY APPARATUS CONTROLLER AND RADIOTHERAPY APPARATUS CONTROL METHOD

BACKGROUND OF THE INVENTION

1. Technical Field

The present invention relates to a radiotherapy apparatus control method and a radiotherapy apparatus controller, and more particularly relates to a radiotherapy apparatus control method and a radiotherapy apparatus controller, which are used when a tumor affected part inside a human body is treated with radiotherapy (radiation therapy).

2. Description of the Related Art

Radiotherapy (radiation therapy) is a known treatment which treats a patient by irradiating a tumor affected part with a therapeutic radiation. A radiotherapy apparatus for executing the radiotherapy includes: an imager system for taking an X-ray image of a patient lying on a couch; and a therapeutic radiation irradiating device for irradiating the patient with the therapeutic radiation. In the radiotherapy apparatus, after the couch is positionally-adjusted so that an affected part of the patient is arranged at a predetermined position based on a CT image of the patient taken in advance and an X-ray image of the patient taken by the imager system immediately before, the therapeutic radiation irradiating device irradiates the affected part with the therapeutic radiation. When the position of the patient is adjusted, it is desired to reduce a feeling of discomfort of the patient.

JP 2006-51215A discloses a treatment table for a radiotherapy apparatus on which a position of an affected part is accurately adjusted. The treatment table for the radiotherapy apparatus includes a support table and a top board, which is attached onto an upper portion of the support table and can be arranged at a first position where overlapping with the support table is the largest and a second position where overlapping with the support table is the smallest when it is viewed from a vertical direction. When the patient is placed on the top board, a value of a deflection of the top board is equal between the first position and the second position.

U.S. Pat. No. 7,373,676B2 Specification discloses a patient support apparatus for adjusting a position of a patient. The patient support apparatus can move in parallel to each of three axes which are vertical to each other and rotationally move around each of the three axes.

SUMMARY OF THE INVENTION

A subject of the present invention is to provide a radiotherapy apparatus controller and a radiotherapy apparatus control method which reduce a feeling of discomfort of a patient when the position of the patient is adjusted.

Another subject of the present invention is to provide a radiotherapy apparatus controller and a radiotherapy apparatus control method which reduce the burden of a patient when the position of the patient is adjusted.

Still another subject of the present invention is to provide a radiotherapy apparatus controller and a radiotherapy apparatus control method which reduce a height of a couch where a patient lies when a patient is treated with radiotherapy.

A radiotherapy apparatus controller of the present invention includes: a planning-stage position data collecting section; a position-adjusting-stage position data collecting section; a correction amount calculating section; a treatment plan collecting section; and an irradiation head driving section. The planning-stage position data collecting section collects planning-stage position data which indicates a planning-stage position where a subject is arranged during a planning stage. The position-adjusting-stage position data collecting section measures position-adjusting-stage 3-dimensional data which indicates a position-adjusting-stage position where the subject is arranged during a position-adjusting stage different from the planning stage. The correction amount calculating section calculates a treatment-stage position, a gantry-angle offset value, a ring-angle offset value based on the planning-stage position data and the position-adjusting-stage 3-dimensional data. The treatment plan collecting section collects an irradiation direction in which an irradiation head is arranged with respect to the planning-stage position, the irradiation head being supported by a gantry, the gantry being supported rotatably with respect to a ring, and the ring being supported rotatably with respect to a base. The irradiation direction indicates a gantry angle and a ring angle. The irradiation head driving section controls an irradiation head driving device, which moves the ring and the gantry, based on the irradiation direction such that the ring is arranged at a corrected ring angle with respect to the base and the gantry is arranged at a corrected gantry angle with respect to the ring. The corrected ring angle indicates the difference that the ring-angle offset value is subtracted from the ring angle. The corrected gantry angle indicates the difference that the gantry-angle offset value is subtracted from the gantry angle. The gantry-angle offset value and the ring-angle offset value are calculated such that the irradiation head is arranged in the irradiation direction with respect to the treatment-stage position when the ring is arranged at the corrected ring angle with respect to the base and the gantry is arranged at the corrected gantry angle with respect to the ring.

This radiotherapy apparatus controller can calculate the treatment-stage position such that a rotational movement amount of which the subject is rotationally moved is reduced or the treatment-stage position is contained in a predetermined range when the subject is moved from the position-adjusting stage position to the treatment-stage position. Therefore, this radiotherapy apparatus controller can reduce a feeling of discomfort of the subject when the subject is moved from the position-adjusting stage position to the treatment-stage position or when the subject is arranged at the treatment-stage position.

The radiotherapy apparatus controller of the present invention may preferably further include an irradiating section controlling the irradiation head such that the irradiation head irradiates the subject with a therapeutic radiation after the subject is arranged at the treatment-stage position, the ring is arranged at the corrected ring angle with respect to the base and the gantry is arranged at the corrected gantry angle with respect to the ring.

The radiotherapy apparatus controller of the present invention may preferably further include a couch driving section controlling a couch driving device which moves the subject such that the subject is moved from the position-adjusting-stage position to the treatment-stage position.

The movement of the subject from the position-adjusting-stage position to the treatment-stage position is formed of a rotational movement rotating around a rotational axis parallel to a direction fixed with respect to the base and a parallel movement with respect to the base. That is, the treatment-stage position is calculated such that the movement of the subject from the position-adjusting-stage position to the treatment-stage position is formed of the rotational movement rotating around the rotational axis parallel to the direction fixed with respect to the base and the parallel movement with respect to the base. According to this radiotherapy apparatus controller, the couch driving device, which moves the couch and the couch supports the subject, is formed such that the couch rotates around single rotational axis only. This makes the couch driving device more inexpensive and more compact than another couch driving device which includes a mechanism that a couch rotates around each of a plurality of axes. At this time, a height of the couch can be reduced and thus a burden of the subject can be reduced when the subject gets on the couch.

The couch driving device includes: a first frame supported parallel-movably with respect to the base; a second frame supported rotatably around a first rotation axis with respect to the first frame; a rotational movement driving device moving a guide in parallel to a first direction with respect to the first frame; a slider supported by the guide movably in parallel to a second direction different from the first direction; and a parallel movement driving device moving the second frame in parallel with respect to the base. At that time, the slider is supported by the second frame rotatably around a second rotation axis different from the first rotation axis.

The position-adjusting-stage 3-dimensional data may preferably indicate a perspective image taken by an imager system supported by the gantry.

The planning-stage position data may preferably indicate 3-dimensional data measured by another modality different form the imager system.

The treatment-stage position may preferably calculate such that the corrected ring angle coincides with the ring angle. Or, the treatment-stage position may preferably calculate such that the corrected gantry angle coincides with the gantry angle.

A radiotherapy apparatus control method of the present invention includes: collecting planning-stage position data which indicates a planning-stage position where a subject is arranged during a planning stage; collecting position-adjusting-stage 3-dimensional data which indicates a position-adjusting-stage position where the subject is arranged during a position-adjusting stage different from the planning stage; calculating a treatment-stage position, a gantry-angle offset value and a ring-angle offset value based on the planning-stage position data and the position-adjusting-stage 3-dimensional data; collecting an irradiation direction in which an irradiation head is arranged with respect to the planning-stage position, the irradiation head being supported by a gantry, the gantry being supported rotatably with respect to a ring, and the ring being supported rotatably with respect to a base; and moving the ring and the gantry such that the ring is arranged at a corrected ring angle with respect to the base and the gantry is arranged at a corrected gantry angle with respect to the ring. The irradiation direction indicates a gantry angle and a ring angle. The corrected ring angle indicates the difference that the ring-angle offset value is subtracted from the ring angle. The corrected gantry angle indicates the difference that the gantry-angle offset value is subtracted from the gantry angle. The gantry-angle offset value and the ring-angle offset value are calculated such that the irradiation head is arranged in the irradiation direction with respect to the treatment-stage position when the ring is arranged at the corrected ring angle with respect to the base and the gantry is arranged at the corrected gantry angle with respect to the ring. This radiotherapy apparatus controlling method can calculates the treatment-stage position such that a rotational movement amount of which the subject is rotationally moved is reduced or the treatment-stage position is contained in a predetermined range when the subject is moved from the position-adjusting stage position to the treatment-stage position. Therefore, this radiotherapy apparatus controlling method can reduce a feeling of discomfort of the subject when the subject is moved from the position-adjusting stage position to the treatment-stage position or when the subject is arranged at the treatment-stage position.

The movement of the subject from the position-adjusting-stage position to the treatment-stage position is formed of a rotational movement rotating around a rotational axis parallel to a direction fixed with respect to the base and a parallel movement with respect to the base. That is, the treatment-stage position is calculated such that the movement of the subject from the position-adjusting-stage position to the treatment-stage position is formed of the rotational movement rotating around the rotational axis parallel to the direction fixed with respect to the base and the parallel movement with respect to the base. According to this radiotherapy apparatus controller, the couch driving device, which moves the couch and the couch supports the subject, is formed such that the couch rotates around single rotational axis only. This makes the couch driving device more inexpensive and more compact than another couch driving device which includes a mechanism that a couch rotates around each of a plurality of axes. As a result, according to this radiotherapy apparatus control method, a height of the couch can be reduced and thus a burden of the subject can be reduced when the subject gets on the couch.

The position-adjusting-stage 3-dimensional data may preferably indicate a perspective image taken by an imager system supported by the gantry.

The planning-stage position data may preferably indicate 3-dimensional data measured by another modality different form the imager system.

The treatment-stage position may preferably calculate such that the corrected ring angle coincides with the ring angle. Or, the treatment-stage position may preferably calculate such that the corrected gantry angle coincides with the gantry angle.

A computer-readable recording medium of the present invention may preferably record a computer program that, when executed, causes a computer to perform the radiotherapy apparatus control method of the present invention.

The radiotherapy apparatus controller and the radiotherapy apparatus control method of the present invention can reduce the rotational movement amount of which the subject is rotationally moved or arrange the subject in the predetermined direction when the position of the patient is adjusted.

DETAILED DESCRIPTION OF THE INVENTION

Figure 1:
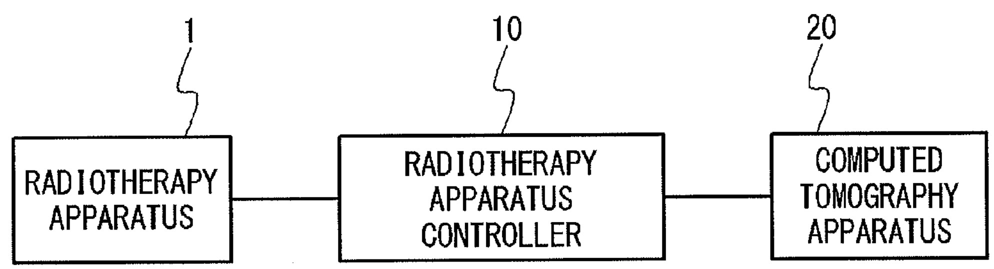
FIG. 1 is a block diagram showing a radiotherapy system.
Figure 2:
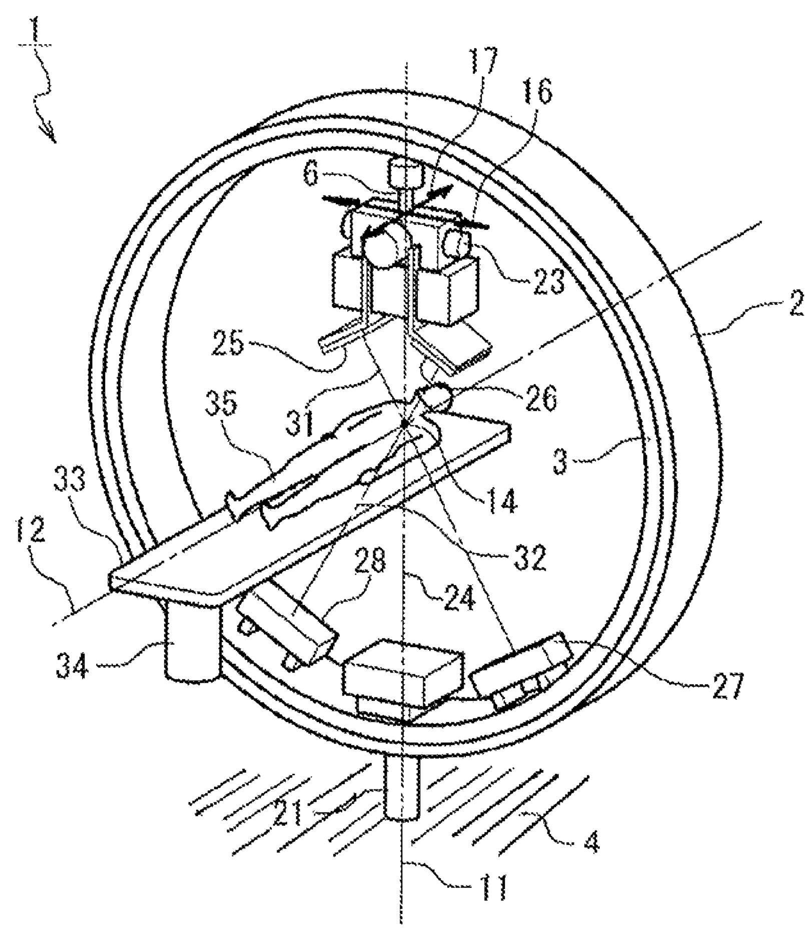
FIG. 2 is a perspective view showing a radiotherapy apparatus.

An embodiment of a radiotherapy apparatus controller according to the present invention will be described below with reference to the drawings. The radiotherapy apparatus controller 10 is applied to a radiotherapy system, as shown in FIG. 1. The radiotherapy system includes a radiotherapy apparatus 1, the radiotherapy apparatus controller 10 and a computed tomography apparatus 20. The radiotherapy apparatus controller 10 is connected to the radiotherapy apparatus 1 and the computed tomography apparatus 20 so that information can be transmitted bi-directionally.

The computed tomography apparatus 20 irradiates a subject with X-rays from respective directions to take a plurality of perspective images, performs image-processing of the plurality of perspective images by using a computer to create cross sectional images of the subject, and performs image-processing of the plurality of perspective images by using the computer to create 3-dimensional data that indicates a state inside the subject. The 3-dimensional data indicates degrees that the X-rays are absorbed by a plurality of sites constituting the subject. The plurality of voxels corresponds to a plurality of regions, respectively, a space where the subject is arranged being filled with the plurality of regions without any gap. For example, each of the plurality of regions is formed as a cuboid. One CT value (Computed Tomography number) corresponding to an arbitrary voxel among the plurality of CT values corresponds to a transmission coefficient (X-ray absorption coefficient) of a region corresponding to the arbitrary voxel in the plurality of regions. That is, an intensity $I_1$ of the X-ray transmitted through the region is represented by the following equation by using its transmission coefficient λ:

$$I_1 = I_o e^{-\lambda x}$$

Here, $I_o$ indicates an intensity before the X-ray comes in the region. A valuable x indicates a thickness of the region.

The radiotherapy apparatus 1 includes: an O-ring 2, a running gantry 3 and a therapeutic radiation irradiating device 6. The O-ring 2 is ring-shaped and supported on a ring base 4 so that the O-ring 2 can be rotated around a ring rotation axis 11. The ring rotation axis 11 is parallel to a vertical direction. The running gantry 3 is ring-shaped. The running gantry 3 is arranged inside a ring of the O-ring 2 and supported by the O-ring 2 so that the running gantry 3 can be rotated around a gantry rotation axis 12. The gantry rotation axis 12 is perpendicular to the vertical direction and intersects the ring rotation axis 11 at an isocenter 14. The gantry rotation axis 12 is fixed with respect to the O-ring 2. That is, the gantry rotation axis 12 is rotated together with the O-ring 2 around the ring rotation axis 11.

The therapeutic radiation irradiating device 6 is arranged inside a ring of the running gantry 3. The therapeutic radiation irradiating device 6 is supported by the running gantry 3 so that the therapeutic radiation irradiating device 6 can be rotated around a tilt axis 16 and rotated around a pan axis 17. The tilt axis 16 is orthogonal to the pan axis 17. The intersection of the tilt axis 16 and the pan axis 17 is 1 m away from the isocenter 14. The therapeutic radiation irradiating device 6 is controlled by the radiotherapy apparatus controller 10 and consequently emits a therapeutic radiation 24 whose irradiation field is controlled. The therapeutic radiation 24 is emitted from a virtual point radiation source possessed by the therapeutic radiation irradiating device 6 and is a conically-shaped cone beam in which the virtual point radiation source serves as an apex. The virtual point radiation source is arranged at the intersection of the tilt axis 16 and the pan axis 17.

The radiotherapy apparatus 1 further includes a ring driving device 21 and a gimbal device 23, and includes a gantry driving device that is not shown. The ring driving device 21 is controlled by the radiotherapy apparatus controller 10 and consequently rotates the O-ring 2 around the ring rotation axis 11. The ring driving device 21 further measures a ring angle at which the O-ring 2 is arranged with respect to the base and outputs the ring angle to the radiotherapy apparatus controller 10. The gantry driving device is controlled by the radiotherapy apparatus controller 10 and consequently rotates the running gantry 3 around the gantry rotation axis 12. The gantry driving device further measures a gantry angle at which the running gantry 3 is arranged with respect to the O-ring 2 and outputs the gantry angle to the radiotherapy apparatus controller 10.

The gimbal device 23 is controlled by the radiotherapy apparatus controller 10 and consequently rotates the therapeutic radiation irradiating device 6 around the tilt axis 16 and rotates the therapeutic radiation irradiating device 6 around the pan axis 17. The gimbal device 23 further measures a tilt angle at which the therapeutic radiation irradiating device 6 is rotated with respect to the running gantry 3 around the tilt axis 16 and outputs the tilt angle to the radiotherapy apparatus controller 10. The gimbal device 23 further measures a pan angle at which the therapeutic radiation irradiating device 6 is rotated with respect to the running gantry 3 around the pan axis 17 and outputs the pan angle to the radiotherapy apparatus controller 10.

The therapeutic radiation irradiating device 6 is supported by the running gantry 3, as mentioned above. Thus, once the therapeutic radiation irradiating device 6 is fixed to the running gantry 3 so as to be oriented to the isocenter 14, the therapeutic radiation 24 is always substantially outputted to the isocenter 14, even if the O-ring 2 is rotated by the ring driving device 21 or even if the running gantry 3 is rotated by the gantry driving device. That is, by carrying out running and turning operations, the radiotherapy apparatus 1 can emit the therapeutic radiation 24 from any direction to the isocenter 14.

The radiotherapy apparatus 1 further includes a plurality of imager systems. That is, the radiotherapy apparatus 1 includes: a first diagnostic radiation irradiating device 25; a second diagnostic radiation irradiating device 26; a first image taking device 27 and a second image taking device 28. The first diagnostic radiation irradiating device 25 is supported by the running gantry 3 and arranged inside the ring of the running gantry 3 so that an angle between a line connecting the isocenter 14 and the first diagnostic radiation irradiating device 25 and a line connecting the isocenter 14 and the therapeutic radiation irradiating device 6 is an acute angle. The second diagnostic radiation irradiating device 26 is supported by the running gantry 3 and arranged inside the ring of the running gantry 3 so that an angle between a line connecting the isocenter 14 and the second diagnostic radiation irradiating device 26 and a line connecting the isocenter 14 and the therapeutic radiation irradiating device 6 is an acute angle. The second diagnostic radiation irradiating device 26 is further arranged so that an angle between a line connecting the isocenter 14 and the first diagnostic radiation irradiating device 25 and a line connecting the isocenter 14 and the second diagnostic radiation irradiating device 26 is a right angle (90 degrees).

The first diagnostic radiation irradiating device 25 is controlled by the radiotherapy apparatus controller 10 and consequently outputs a first diagnostic radiation 31 to the isocenter 14 at a predetermined timing. The first diagnostic radiation 31 is outputted from a virtual point radiation source possessed by the first diagnostic radiation irradiating device 25 and is a conically-shaped cone beam whose apex is the virtual point radiation source. The second diagnostic radiation irradiating device 26 is controlled by the radiotherapy apparatus controller 10 and consequently outputs a second diagnostic radiation 32 to the isocenter 14 at a predetermined timing. The second diagnostic radiation 32 is outputted from a virtual point radiation source possessed by the second diagnostic radiation irradiating device 26 and is a conically-shaped cone beam whose apex is the virtual point radiation source.

The first image taking device 27 includes a light receiving unit. The first image taking device 27 is controlled by the radiotherapy apparatus controller 10 and consequently creates a first perspective image based on the X-ray received by the light receiving unit. As the first image taking device 27, FPD (Flat Panel Detector) and X-ray II (Image Intensifier) are exemplified. The first image taking device 27 is supported by the running gantry 3 and arranged so as to take a perspective image in which the isocenter 14 is projected at the center via the first diagnostic radiation 31. That is, the first image taking device 27 is arranged such that the center of the light receiving unit of the first image taking device 27, the virtual point radiation source from which the first diagnostic radiation 31 is emitted and the isocenter 14 are arranged on a straight line.

The second image taking device 28 includes a light receiving unit. The second image taking device 28 is controlled by the radiotherapy apparatus controller 10 and consequently creates a second perspective image based on the X-ray received by the light receiving unit. As the second image taking device 28, FPD (Flat Panel Detector) and X-ray II (Image Intensifier) are exemplified. The second image taking device 28 is supported by the running gantry 3 and arranged so as to take a perspective image in which the isocenter 14 is projected at the center via the second diagnostic radiation 32. That is, the second image taking device 28 is arranged such that the center of the light receiving unit of the second image taking device 28, the virtual point radiation source from which the second diagnostic radiation 32 is emitted and the isocenter 14 are arranged on a straight line.

The perspective image is formed by a plurality of pixels. The plurality of pixels is arranged in a matrix shape on the perspective image and each of the plurality of pixels is correlated to its brightness. Each of the plurality of pixels is colored a color corresponding to its brightness, and thus a subject is projected on the perspective image.

The radiotherapy apparatus 1 further includes a couch 33 and a couch driving device 34. The couch 33 is supported on the base so that the couch 33 can be moved parallel to the X-axis, the Y-axis and the Z-axis and rotated around the X-axis. The X-axis, the Y-axis and the Z-axis are orthogonal to each other. The couch 33 is used for a patient 35 in a lying position, who is being treated with the radiotherapy system. The couch 33 includes a fixing tool that is not shown. The fixing tool fixes the patient 35 onto the couch 33 so that the patient 35 cannot move. The couch driving device 34 is controlled by the radiotherapy apparatus controller 10 and consequently rotationally moves the couch 33 and parallel-moves the couch 33.

Figure 3:
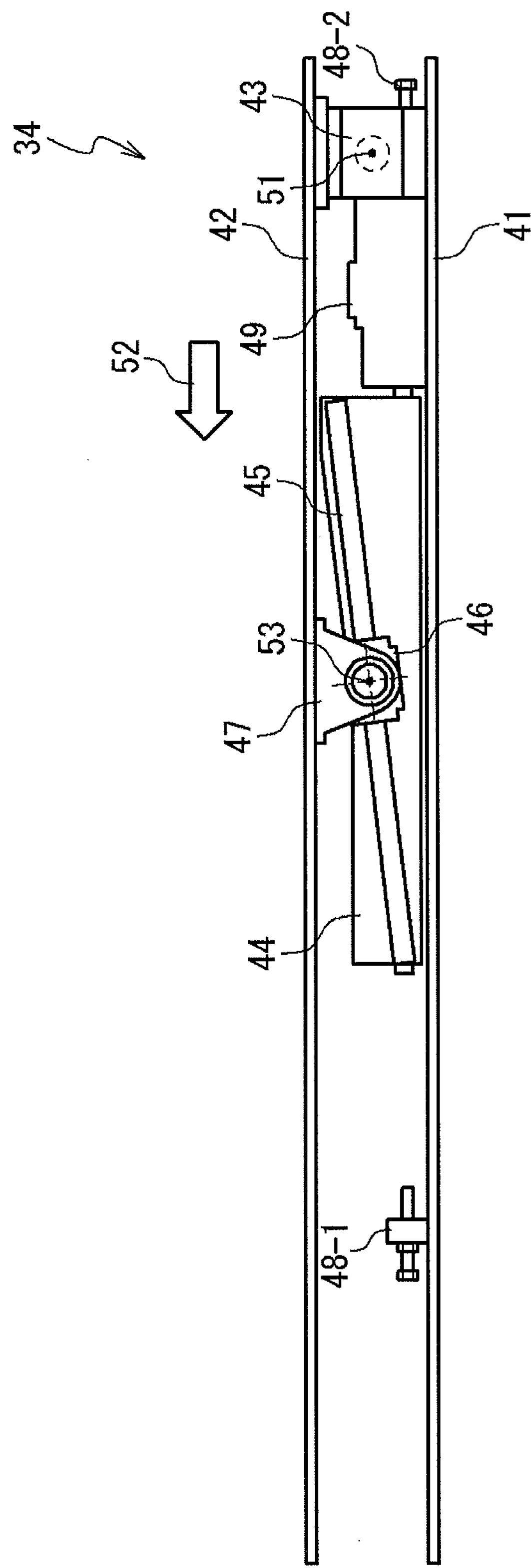
FIG. 3 is a plan view showing a couch driving device.

FIG. 3 shows the couch driving device 34. The couch driving device 34 includes a frame 41 and a top board supporting part 42. The frame 41 is plate-shaped. The frame 41 is supported on the base so that the frame 41 can be moved in parallel to the base. The top board supporting part 42 is plate-shaped and fixed to the couch 33. The top board supporting part 42 is supported by the frame 41 so that the top board supporting part 42 can be rotated around a rotation axis 51 through a bearing 43. The rotation axis 51 is perpendicular to the ring rotation axis 11.

The couch driving device 34 further includes a movable frame 44, an inclination direct-acting guide 45 and a slider 46. The movable frame 44 is supported by the frame 41 so that the movable frame 44 can be moved in parallel to an O-ring-opposite direction 52. The O-ring-opposite direction 52 is perpendicular to the rotation axis 51 and perpendicular to the ring rotation axis 11. The inclination direct-acting guide 45 is bar-shaped and fixed to the movable frame 44. The slider 46 is supported by the inclination direct-acting guide 45 so that the slider 46 can be parallel-moved along the inclination direct-acting guide 45. The slider 46 is supported by the top board supporting part 42 so that the slider 46 can be rotated around a rotation axis 53 through a bearing 47.

The couch driving device 34 further includes stoppers 48-1 to 48-2 and a rotational movement driving device 49. The stopper 48-1 is fixed to and arranged in the frame 41 so that the stopper 48-1 is brought into contact with the movable frame 44 when the movable frame 44 is arranged at a predetermined position. That is, the stopper 48-1 limits the movable range of the movable frame 44 so that the movable frame 44 does not move in the O-ring-opposite direction 52 beyond the predetermined position. The stopper 48-2 is fixed to and arranged in the frame 41 so that the stopper 48-2 is brought into contact with the movable frame 44 when the movable frame 44 is arranged at a predetermined position. That is, the stopper 48-2 limits the movable range of the movable frame 44 so that the movable frame 44 does not move in the O-ring-opposite direction 52 beyond the predetermined position. The rotational movement driving device 49 is controlled by the radiotherapy apparatus controller 10 and consequently moves the movable frame 44 in parallel to the O-ring-opposite direction 52 with respect to the frame 41.

The couch driving device 34 further includes a parallel movement driving device that is not shown. The parallel movement driving device is controlled by the radiotherapy apparatus controller 10 and consequently parallel-moves the frame 41 with respect to the base. That is, the parallel movement driving device is controlled by the radiotherapy apparatus controller 10 and consequently parallel-moves the top board supporting part 42 with respect to the base and parallel-moves the couch 33 with respect to the base.

Figure 4:
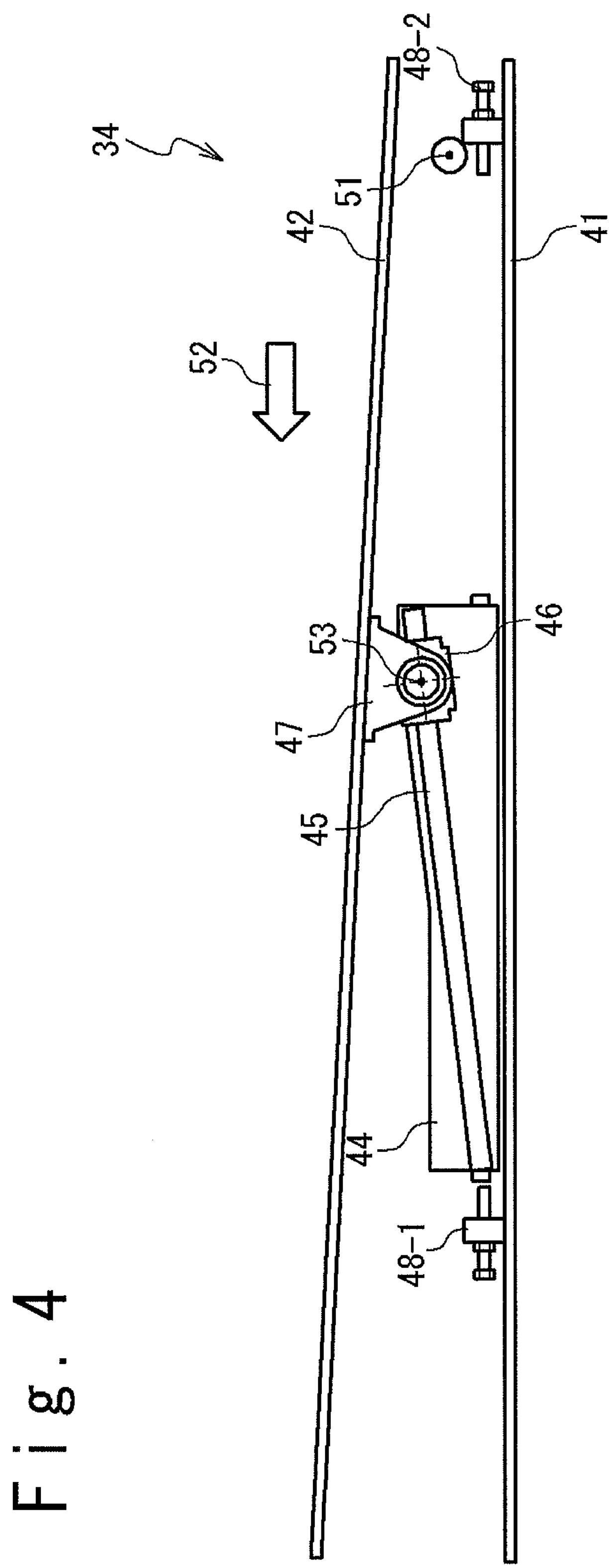
FIG. 4 is a plan view showing another state of the couch driving device.

FIG. 4 shows a state of the couch driving device 34 when the movable frame 44 is parallel-moved in the O-ring-opposite direction 52. When the movable frame 44 is parallel-moved in the O-ring-opposite direction 52, the slider 46 is guided by the inclination direct-acting guide 45 and moved away from the frame 41. When the slider 46 is moved away from the frame 41, the top board supporting part 42 is rotated clockwise around the rotation axis 51.

Figure 5:
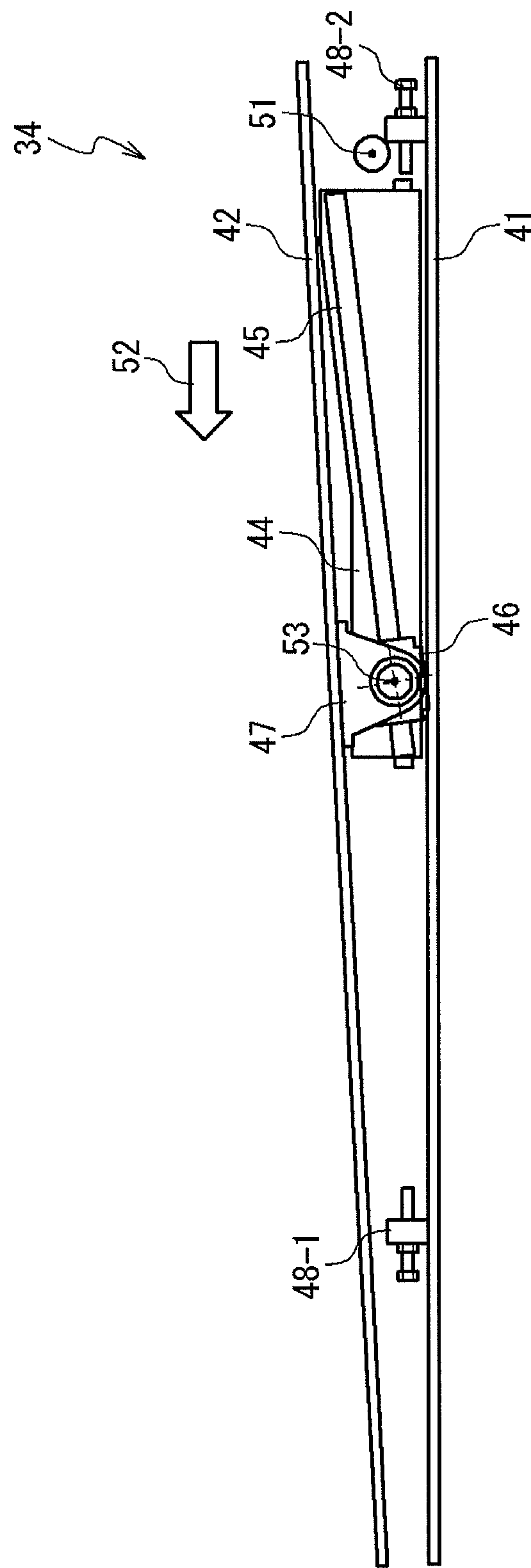
FIG. 5 is a plan view showing still another state of the couch driving device.

FIG. 5 shows a state of the couch driving device 34 when the movable frame 44 is parallel-moved in a direction opposite to the O-ring-opposite direction 52. When the movable frame 44 is parallel-moved in the direction opposite to the O-ring-opposite direction 52, the slider 46 is guided by the inclination direct-acting guide 45 and moved closer to the frame 41. When the slider 46 is moved closer to the frame 41, the top board supporting part 42 is rotated counterclockwise around the rotation axis 51.

The foregoing couch driving device 34 is more compact as compared with a different couch driving device that can rotationally move the couch 33 around a plurality of rotation axes, which are not parallel to each other. For this reason, according to the couch driving device 34, since the height of the couch 33 can be made lower, a burden of the patient 35 can be reduced when the patient 35 who is treated with radiotherapy gets on the couch 33.

Figure 6:
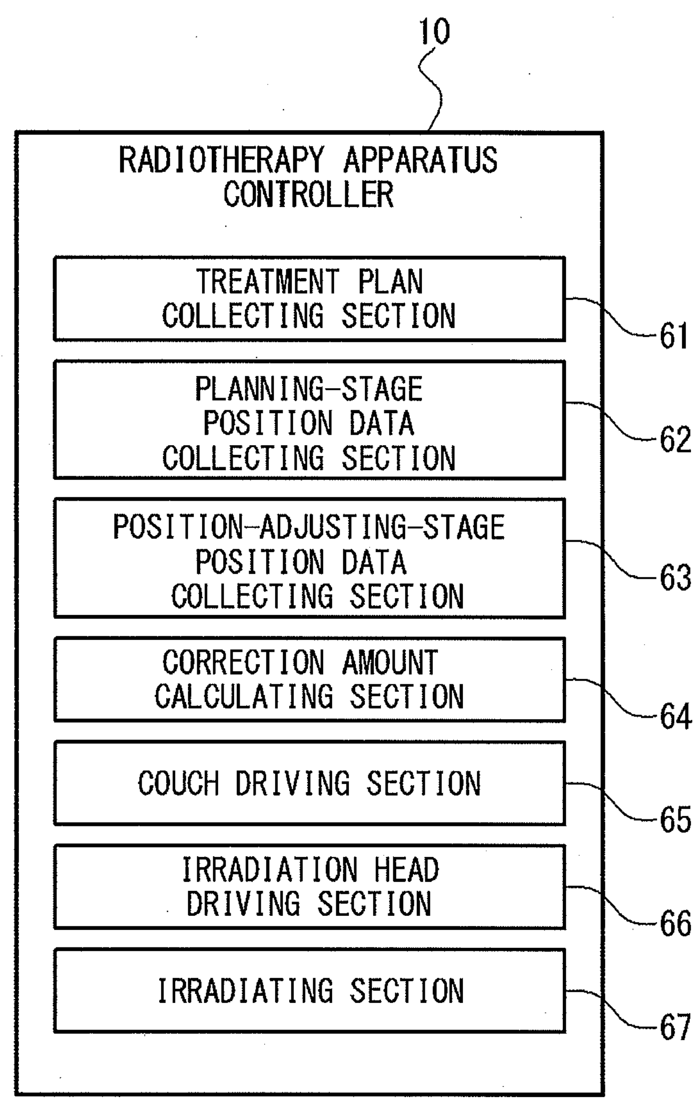
FIG. 6 is a block diagram showing a radiotherapy apparatus controller.

FIG. 6 shows the radiotherapy apparatus controller 10. The radiotherapy apparatus controller 10 is a computer including: a CPU; a storage unit, a removable memory drive, a communication unit, an input unit, an output unit and an interface, which are not shown. The CPU executes a computer program installed in the radiotherapy apparatus controller 10 and controls the storage unit, the removable memory drive, the communication unit, the input unit, the output unit and the interface. The storage unit records the computer program. The storage unit further records information used by the CPU. The removable memory drive is used for installing the computer program into the radiotherapy apparatus controller 10 when a recording medium in which the computer program is recorded is inserted. The communication unit is used for downloading the computer program from another computer, which is connected through a communication network to the radiotherapy apparatus controller 10, to the radiotherapy apparatus controller 10 to install the computer program into the radiotherapy apparatus controller 10. The input unit outputs information, which is created by operation of a user, to the CPU. As the input unit, a keyboard and a mouse are exemplified. The output unit outputs information created by the CPU recognizably to the user. As the output unit, a display for displaying images created by the CPU is exemplified.

The interface outputs information, which is created by external devices connected to the radiotherapy apparatus controller 10, to the CPU and outputs information created by the CPU to the external devices. The external devices includes: the computed tomography apparatus 20; the therapeutic radiation irradiating device 6, the ring driving device 21, the gantry driving device, the gimbal device 23, the first diagnostic radiation irradiating device 25, the second diagnostic radiation irradiating device 26, the first image taking device 27, the second image taking device 28 and the couch driving device 34.

The computer program installed in the radiotherapy apparatus controller 10 is provided with a plurality of computer programs for attaining a plurality of functions in the radiotherapy apparatus controller 10, respectively. The plurality of functions includes: a treatment plan collecting section 61, a planning-stage position data collecting section 62, a position-adjusting-stage position data collecting section 63, a correction amount calculating section 64, a couch driving section 65, an irradiation head driving section 66 and an irradiating section 67.

The treatment plan collecting section 61 collects a treatment plan from the input unit. The treatment plan is created based on the 3-dimensional data of the patient 35 that is taken by the computed tomography apparatus 20 and indicates an emitting condition. The emitting condition indicates an emitting direction and a radiation dose. The emitting direction indicates a direction in which the therapeutic radiation 24 is emitted to the patient 35 and indicates a ring angle and a gantry angle. The ring angle indicates a position at which the O-ring 2 is arranged with respect to the base. The gantry angle indicates a position at which the running gantry 3 is arranged with respect to the O-ring 2. The radiation dose indicates a dose of the therapeutic radiation 24 that is emitted to the patient 35 from the emitting direction.

The planning-stage position data collecting section 62 collects 3-dimensional data, which is used when the treatment plan collected by the treatment plan collecting section 61 is created, from the computed tomography apparatus 20. In the 3-dimensional data, a plurality of CT values is correlated to a plurality of voxels. The planning-stage position data collecting section 62 calculates a planning-stage position based on the 3-dimensional data. The planning-stage position indicates a position and an orientation where the patient 35 is arranged when the plurality of perspective images is taken by the computed tomography apparatus 20 in reconfiguring the 3-dimensional data. At this time, the emitting direction indicated by the treatment plan indicates a direction in which the therapeutic radiation 24 is emitted to the patient 35 arranged at the planning-stage position.

The position-adjusting-stage position data collecting section 63 controls the radiotherapy apparatus 1 so that a position-adjusting-stage first perspective image and a position-adjusting-stage second perspective image in which the patient 35 lying on the couch 33 is projected are taken. That is, the position-adjusting-stage position data collecting section 63 controls the couch driving device 34 so that the couch 33 is arranged at a proper position with respect to the base, when the patient 35 is fixed to the couch 33. The position-adjusting-stage position data collecting section 63 further controls the ring driving device 21 so that the O-ring 2 is arranged at a proper ring angle with respect to the base. The position-adjusting-stage position data collecting section 63 further controls the gantry driving device in the radiotherapy apparatus 1 so that the running gantry 3 is arranged at a proper gantry angle with respect to the O-ring 2.

The position-adjusting-stage position data collecting section 63 further controls the first diagnostic radiation irradiating device 25 so that the first diagnostic radiation 31 is emitted, when the O-ring 2 and the running gantry 3 are arranged at proper positions. The position-adjusting-stage position data collecting section 63 further controls the first image taking device 27 so that the position-adjusting-stage first perspective image is created based on an X-ray transmitted through the patient 35, when the first diagnostic radiation 31 is emitted to the patient 35. Brightness, which corresponds to an arbitrary pixel among a plurality of brightness indicated by the position-adjusting-stage first perspective image, corresponds to a transmission coefficient that an X-ray is transmitted through a physical body arranged on a line connecting the first diagnostic radiation irradiating device 25 and a region corresponding to the arbitrary pixel in the light receiving unit of the first image taking device 27.

The position-adjusting-stage position data collecting section 63 further controls the second diagnostic radiation irradiating device 26 so that the second diagnostic radiation 32 is emitted, when the O-ring 2 and the running gantry 3 are arranged at proper positions. The position-adjusting-stage position data collecting section 63 further controls the second image taking unit 28 so that the position-adjusting-stage second perspective image is created based on an X-ray transmitted through the patient 35, when the second diagnostic radiation 32 is emitted to the patient 35. Brightness, which corresponds to an arbitrary pixel among a plurality of brightness indicated by the position-adjusting-stage second perspective image, corresponds to a transmission coefficient that an X-ray is transmitted through a physical body arranged on a line connecting the second diagnostic radiation irradiating device 26 and a region corresponding to the arbitrary pixel in the light receiving unit of the second image taking device 28.

The position-adjusting-stage position data collecting section 63 further calculates a position-adjusting-stage position based on the position-adjusting-stage first perspective image and the position-adjusting-stage second perspective image. The position-adjusting-stage position indicates a position and an orientation where the patient 35 is arranged when the position-adjusting-stage first perspective image and the position-adjusting-stage second perspective image are taken.

The correction amount calculating section 64 calculates a patient position, a ring-angle offset value and a gantry-angle offset value based on a planning-stage position calculated by the planning-stage position data collecting section 62 and the position-adjusting-stage position calculated by the position-adjusting-stage position data collecting section 63.

The patient position indicates a position and an orientation where the patient 35 is arranged and indicates a position and an orientation where the patient 35 can be moved by the couch driving device 34 from the position where the patient 35 is arranged when the position-adjusting-stage first perspective image and the position-adjusting-stage second perspective image are taken. That is, the patient position is calculated such that the patient 35, who is arranged at the position-adjusting-stage position calculated by the position-adjusting-stage position data collecting section 63, can be moved to the patient position by the parallel movement and the rotational movement rotating around the rotation axis 51.

The ring-angle offset value indicates a difference that a treating-stage ring angle is subtracted from a planning-stage ring angle. The gantry-angle offset value indicates a difference that a treating-stage gantry angle is subtracted from a planning-stage gantry angle. At this time, a treating-stage orientation in which the therapeutic radiation irradiating device 6 is arranged with respect to the patient position, when the O-ring 2 is arranged at the treating-stage ring angle with respect to the base and the running gantry 3 is arranged at the treating-stage gantry angle with respect to the O-ring 2, coincides with a planning-stage orientation in which the therapeutic radiation irradiating device 6 is arranged with respect to the planning-stage position, when the O-ring 2 is arranged at the planning-stage ring angle with respect to the base and the running gantry 3 is arranged at the planning-stage gantry angle with respect to the O-ring 2. That is, the gantry-angle offset value and the ring-angle offset value are calculated such that the treating-stage orientation coincides with the planning-stage orientation.

The couch driving section 65 controls the couch driving device 34 so that the patient 35 who is arranged at the position-adjusting-stage position calculated by the position-adjusting-stage position data collecting section 63 is moved to the patient position based on the patient position calculated by the correction amount calculating section 64. That is, the couch driving section 65 controls the rotational movement driving device 49 so that the patient 35 is oriented to the direction indicated by the patient position and controls the parallel movement driving device of the couch driving device 34 so that the patient 35 is arranged at the position indicated by the patient position.

The irradiation head driving section 66 controls the radiotherapy apparatus 1 based on the emitting direction indicated by the treatment plan collected by the treatment plan collecting section 61. That is, the irradiation head driving section 66 controls the ring driving device 21 so that the O-ring 2 is arranged at a corrected ring angle with respect to the base. The irradiation head driving section 66 further controls the gantry driving device of the radiotherapy apparatus 1 so that the running gantry 3 is arranged at a corrected gantry angle with respect to the O-ring 2. The corrected ring angle indicates a value in which the ring-angle offset value calculated by the correction amount calculating section 64 is subtracted from the ring angle indicated by the emitting direction. The corrected gantry angle indicates a value in which the gantry-angle offset value calculated by the correction amount calculating section 64 is subtracted from the gantry angle indicated by the emitting condition.

The irradiating section 67 controls the radiotherapy apparatus 1 so that a treating-stage first perspective image and a treating-stage second perspective image in which the affected part of the patient 35 is projected are taken after the patient 35 is arranged at the patient position by the couch driving section 65 and the therapeutic radiation irradiating device 6 is arranged at a predetermined position by the irradiation head driving section 66. That is, the irradiating section 67 controls the first diagnostic radiation irradiating unit 25 so that the first diagnostic radiation 31 is emitted. The irradiating section 67 controls the first image taking device 27 so that the treating-stage first perspective image is taken. The irradiating section 67 controls the second diagnostic radiation irradiating unit 26 so that the second diagnostic radiation 32 is emitted. The irradiating section 67 controls the second image taking device 28 so that the treating-stage second perspective image is taken.

The irradiating section 67 further calculates a position of the affected part of the patient 35 and calculates a shape of the affected part, based on the treating-stage first perspective image and the treating-stage second perspective image. The irradiating section 67 further controls the gimbal device 23 so that the therapeutic radiation irradiating device 6 is oriented to the calculated position of the affected part. The irradiating section 67 further controls the therapeutic radiation irradiating device 6 so that the irradiation field of the therapeutic radiation 24 coincides with the shape of the affected part, and controls the therapeutic radiation irradiating device 6 so that the therapeutic radiation 24 is emitted to the affected part. Moreover, the irradiating section 67 repeatedly executes the operations from the taking of the treating-stage first perspective image and the treating-stage second perspective image to the emitting of the therapeutic radiation 24, until the therapeutic radiation 24 of the does indicated by the emitting condition is emitted to the affected part of the patient 35.

The embodiment of the radiotherapy apparatus control method according to the present invention is executed by the radiotherapy apparatus controller 10 and includes an operation for creating a treatment plan, an operation for adjusting a position of a patient, and an operation for carrying out radiotherapy.

In the operation for creating the treatment plan, at first, a user takes a plurality of perspective images by using the computed tomography apparatus 20, and then creates 3-dimensional data indicating a state inside the patient 35 based on the plurality of perspective images. The 3-dimensional data indicates a planning-stage position. The planning-stage position indicates a position and an orientation where the patient 35 is arranged when the plurality of perspective images is taken. The user further creates treatment plan based on the 3-dimensional data. The treatment plan indicates an emitting condition. The emitting condition indicates an emitting direction and a radiation dose. The emitting direction indicates a planning-stage direction where the therapeutic radiation 24 is arranged correspondingly to the planning-stage position and indicates a ring angle and a gantry angle. The ring angle indicates a position at which the O-ring 2 is arranged with respect to the base. The gantry angle indicates a position at which the running gantry 3 is arranged with respect to the O-ring 2. The radiation dose indicates a dose of the therapeutic radiation 24 that is emitted to the patient 35 from the emitting direction. The user inputs the treatment plan to the radiotherapy apparatus controller 10 through the input unit of the radiotherapy apparatus controller 10.

Figure 7:
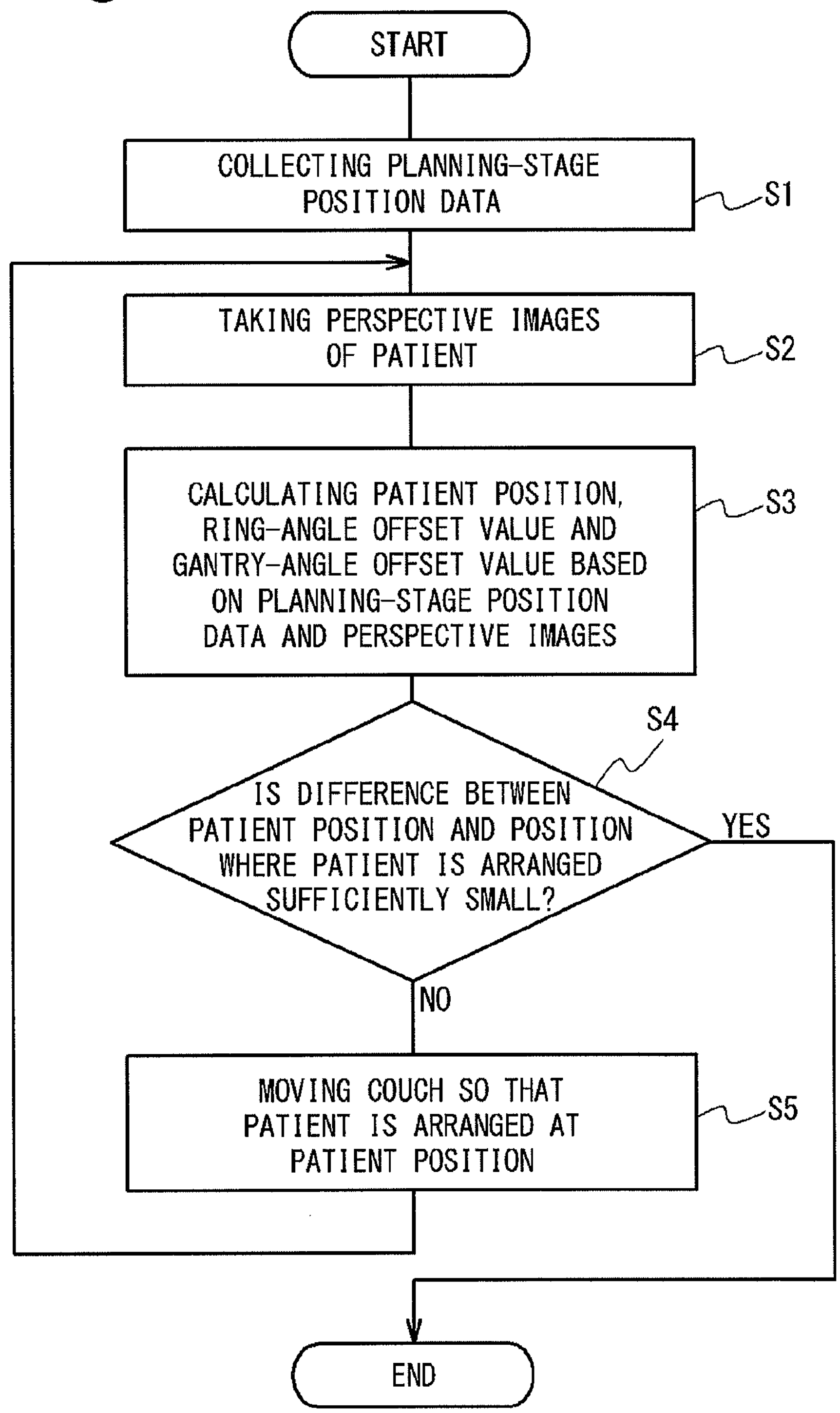
FIG. 7 is a flowchart showing an operation for adjusting a position of a patient.

FIG. 7 shows the operation for adjusting the position of the patient. The operation for adjusting the position of the patient is executed after the execution of the operation for creating the treatment plan, for example, several days after the execution of the operation for creating the treatment plan. The radiotherapy apparatus controller 10 collects the 3-dimensional data used at the time of the creating the treatment plan, from the computed tomography apparatus 20 (Step S1). The radiotherapy apparatus controller 10 calculates the planning-stage position based on the 3-dimensional data.

The patient 35 gets on the couch 33 and lies on the couch 33. After the patient 35 lies on the couch 33, the user uses a fixing tool to fix the patient 35 to the couch 33. After the patient 35 is fixed to the couch 33, the radiotherapy apparatus controller 10 controls the couch driving device 34 so that the affected part of the patient 35 is substantially arranged at the isocenter 14.

The radiotherapy apparatus controller 10 controls the radiotherapy apparatus 1 so that a position-adjusting-stage first perspective image and a position-adjusting-stage-second perspective image, in which the patient 35 lying on the couch 33 is projected, are taken (Step S2). That is, after the patient 35 is fixed to the couch 33, the radiotherapy apparatus controller 10 controls the couch driving device 34 so that the affected part of the patient 35 is substantially arranged at the isocenter 14. The radiotherapy apparatus controller 10 further moves the running gantry 3 to a proper position so that an image of the affected part of the patient 35 is taken by the imager system. That is, the radiotherapy apparatus controller 10 controls the ring driving device 21 so that the O-ring 2 is arranged at a proper ring angle with respect to the base. The radiotherapy apparatus controller 10 further controls the gantry driving device of the radiotherapy apparatus 1 so that the running gantry 3 is arranged at a proper gantry angle with respect to the O-ring 2.

The radiotherapy apparatus controller 10 further controls the first diagnostic radiation irradiating device 25 so that the first diagnostic radiation 31 is emitted when the O-ring 2 and the running gantry 3 are arranged at the proper positions. The radiotherapy apparatus controller 10 further controls the first image taking device 27 so that the position-adjusting-stage first perspective image is created based on the X-ray transmitted through the patient 35 when the first diagnostic radiation 31 is emitted to the patient 35. The radiotherapy apparatus controller 10 further controls the second diagnostic radiation irradiating device 26 so that the second diagnostic radiation 32 is emitted when the O-ring 2 and the running gantry 3 are arranged at the predetermined positions. The radiotherapy apparatus controller 10 further controls the second image taking device 28 so that the position-adjusting-stage second perspective image is created based on the X-ray transmitted through the patient 35 when the second diagnostic radiation 32 is emitted to the patient 35.

The radiotherapy apparatus controller 10 further calculates the position-adjusting-stage position based on the position-adjusting-stage first perspective image and the position-adjusting-stage second perspective image. The position-adjustment-stage position indicates a position and an orientation where the patient 35 is arranged when the position-adjusting-stage first perspective image and the position-adjusting-stage second perspective image are taken.

The radiotherapy apparatus controller 10 calculates the patient position, the ring-angle offset value and the gantry-angle offset value, based on the position-adjusting-stage position and the planning-stage position calculated at the step S1 (Step S3). The patient position indicates a position and an orientation where the patient 35 is arranged and indicates a position and an orientation where the patient 35 can be moved by the couch driving device 34 from the position where the patient 35 is arranged when the position-adjusting-stage first perspective image and the position-adjusting-stage second perspective image are taken. That is, the patient position is calculated such that the patient 35, who is arranged at the position-adjusting-stage position calculated by the radiotherapy apparatus controller 10, can be moved to the patient position by the parallel movement and the rotational movement rotating around the rotation axis 51.

The ring-angle offset value indicates a difference that the treating-stage ring angle is subtracted from the planning-stage ring angle. The gantry-angle offset value indicates a difference that the treating-stage gantry angle is subtracted from the planning-stage gantry angle. At this time, the treating-stage orientation in which the therapeutic radiation irradiating device 6 is arranged with respect to the patient position, when the O-ring 2 is arranged at the treating-stage ring angle with respect to the base and the running gantry 3 is arranged at the treating-stage gantry angle with respect to the O-ring 2, coincides with the planning-stage orientation in which the therapeutic radiation irradiating device 6 is arranged with respect to the planning-stage position, when the O-ring 2 is arranged at the planning-stage ring angle with respect to the base and the running gantry 3 is arranged at the planning-stage gantry angle with respect to the O-ring 2. That is, the gantry-angle offset value and the ring-angle offset value are calculated such that the treating-stage orientation coincides with the planning-stage orientation.

If the difference between the position-adjusting-stage position and the patient position is greater than a predetermined value (Step S4, NO), the radiotherapy apparatus controller 10 controls the couch driving device 34 so that the patient 35 is moved to the patient position (Step S5). That is, the radiotherapy apparatus controller 10 controls the rotational movement driving device 49 so that the patient 35 oriented to an orientation indicated by the position-adjusting-stage position is oriented to an orientation indicated by the patient position. The radiotherapy apparatus controller 10 controls the parallel movement driving device of the couch driving device 34 so that the patient 35 arranged at a position indicated by the position-adjusting-stage position is arranged at a position indicated by the patient position.

The radiotherapy apparatus controller 10, after controlling the couch driving device 34 so that the patient 35 is moved to the patient position, controls the radiotherapy apparatus 1 so that the position-adjusting-stage first perspective image and the position-adjusting-stage second perspective image, in which the patient 35 lying on the couch 33 is projected, are again taken (Step S2). Moreover, the radiotherapy apparatus controller 10 again calculates the position-adjusting-stage position based on the position-adjusting-stage first perspective image and the position-adjusting-stage second perspective image. The radiotherapy apparatus controller 10 again calculates the patient position, the ring-angle offset value and the gantry-angle offset value based on the position-adjusting-stage position and the planning-stage position collected at the step S1 (Step S3).

Until the difference between the position-adjusting-stage position and the patient position becomes smaller than the predetermined value (Step S4, YES), the radiotherapy apparatus controller 10 repeatedly executes the step S5, the step S2 and the step S3.

The operation for performing the radiotherapy is executed just after the execution of the operation for adjusting the position of the patient. The radiotherapy apparatus controller 10 controls the radiotherapy apparatus 1 based on the emitting condition indicated by the treatment plan. That is, the radiotherapy apparatus controller 10 controls the ring driving device 21 so that the O-ring 2 is arranged at the corrected ring angle with respect to the base. The radiotherapy apparatus controller 10 further controls the gantry driving device in the radiotherapy apparatus 1 so that the running gantry 3 is arranged at the corrected gantry angle with respect to the O-ring 2. The corrected ring angle indicates a value in which the ring-angle offset value calculated by the correction amount calculating section 64 is subtracted from the ring angle indicated by the emitting condition. The corrected gantry angle indicates a value in which the gantry-angle offset value calculated by the correction amount calculating section 64 is subtracted from the gantry angle indicated by the emitting condition.

Next, the radiotherapy apparatus controller 10 controls the radiotherapy apparatus 1 so that a treating-stage first perspective image and a treating-stage second perspective image in which the affected part of the patient 35 is projected are taken. That is, the radiotherapy apparatus controller 10 controls the first diagnostic radiation irradiating device 25 so that the first diagnostic radiation 31 is emitted. The radiotherapy apparatus controller 10 controls the first image taking device 27 so that the treating-stage first perspective image is taken. The radiotherapy apparatus controller 10 controls the second diagnostic radiation irradiating device 26 so that the second diagnostic radiation 32 is emitted. The radiotherapy apparatus controller 10 controls the second image taking device 28 so that the treating-stage second perspective image is taken.

The radiotherapy apparatus controller 10 further calculates a position of the affected part of the patient 35 and calculates a shape of the affected part, based on the treating-stage first perspective image and the treating-stage second perspective image. The radiotherapy apparatus controller 10 further controls the gimbal device 23 so that the therapeutic radiation irradiating device 6 is oriented to the calculated position of the affected part. The radiotherapy apparatus controller 10 further controls the therapeutic radiation irradiating device 6 so that an irradiation field of the therapeutic radiation 24 coincides with the shape of the affected part, and controls the therapeutic radiation irradiating device 6 so that the therapeutic radiation 24 is emitted to the affected part. Moreover, the radiotherapy apparatus controller 10 repeatedly executes the operations from the taking of the treating-stage first perspective image and the treating-stage second perspective image to the emitting of the therapeutic radiation 24, until the therapeutic radiation 24 of the dose indicated by the emitting condition is emitted to the affected part of the patient 35.

According to the foregoing radiotherapy, even if the affected part of the patient 35 is moved, the radiotherapy apparatus controller 10 can irradiate the affected part with the therapeutic radiation 24 at a higher precision and can perform the radiotherapy on the patient 35 at a higher precision.

Incidentally, the treatment plan can also indicate a plurality of emitting conditions. At this time, the radiotherapy apparatus controller 10 executes the operation for carrying out the foregoing radiotherapy, for each emitting condition.

According to the foregoing radiotherapy apparatus control method, in the radiotherapy apparatus controller 10, when the position of the patient 35 is adjusted, the couch 33 is not required to be rotationally moved around a rotation axis, which is not parallel to the rotation axis 51. Consequently, for the radiotherapy apparatus 1, it is possible to apply the couch driving device 34 that is more compact than a different couch driving device in which the couch 33 can be rotated around two or three rotation axes. At this time, in the radiotherapy apparatus controller 10, the height of the couch 33 can be made lower, and a burden that the patient 35 gets on the couch 33 can be reduced. In the radiotherapy apparatus controller 10, it is further possible to reduce a feeling of discomfort of the patient 35 that results from the rotation, when the position of the patient 35 is adjusted.

Incidentally, the couch driving device 34 may be replaced with a different couch driving device that can rotate the couch 33 around the two or three rotation axes. Also in this case, in the radiotherapy apparatus controller 10, it is possible to reduce the burden when the patient 35 gets on the couch 33, similarly to the case in which the couch driving device 34 is applied.

When the foregoing couch driving device is applied to the radiotherapy apparatus 1, the correction amount calculating section 64 can also calculate the patient position so that a rotational movement amount for rotationally moving the patient 35 is further reduced at the time of adjusting the position of the patient 35. According to the foregoing calculation of the patient position, in the radiotherapy apparatus controller 10, it is possible to reduce a feeling of discomfort that results from the rotation of the patient 35 lying on the couch 33.

When the couch driving device 34 can further rotate the couch 33 around a different rotation axis parallel to the ring rotation axis 11, based on the planning-stage position calculated by the planning-stage position data collecting section 62 and the position-adjusting-stage position calculated by the position-adjusting-stage position data collecting section 63, the correction amount calculating section 64 can also calculate the patient position and the gantry-angle offset value so that the ring-angle offset value is 0. That is, the gantry-angle offset value indicates a difference in which the treating-stage gantry angle is subtracted from the planning-stage gantry angle. The treating-stage orientation in which the therapeutic radiation irradiating device 6 is arranged with respect to the patient position, when the O-ring 2 is arranged at a certain ring angle with respect to the base and the running gantry 3 is arranged at the treating-stage gantry angle with respect to the O-ring 2, coincides with the planning-stage orientation in which the therapeutic radiation irradiating device 6 is arranged at the planning-stage position, when the O-ring 2 is arranged at the ring angle with respect to the base and the running gantry 3 is arranged at the planning-stage gantry angle with respect to the O-ring 2. That is, the patient position and the gantry-angle offset value are calculated such that the treating-stage orientation coincides with the planning-stage orientation. According to the foregoing patient position, in the radiotherapy apparatus controller 10, when the position of the patient 35 is adjusted, the couch 33 is not required to be rotationally moved around the three rotation axes perpendicular to each other. Consequently, for the radiotherapy apparatus 1, it is possible to apply the two-axes rotation driving device that is more compact than the different couch driving device that can rotate the couch 33 around the three rotation axes. At this time, in the radiotherapy apparatus controller 10, the height of the couch 33 can be made lower, and it is possible to reduce the burden when the patient 35 gets on the couch 33.

When the couch driving device 34 can further rotate the couch 33 around a different rotation axis perpendicular to the ring rotation axis 11 and the rotation axis 51, based on the planning-stage position calculated by the planning-stage position data collecting section 62 and the position-adjusting-stage position calculated by the position-adjusting-stage position data collecting section 63, the correction amount calculating section 64 can also calculate the patient position and the ring-angle offset value so that the gantry-angle offset value is 0. That is, the ring-angle offset value indicates a difference in which the treating-stage ring angle is subtracted from the planning-stage ring angle. The treating-stage orientation in which the therapeutic radiation irradiating device 6 is arranged with respect to the patient position, when the O-ring 2 is arranged at the planning-stage ring angle with respect to the base and the running gantry 3 is arranged at a certain gantry angle with respect to the O-ring 2, coincides with the planning-stage orientation in which the therapeutic radiation irradiating device 6 is arranged at the planning-stage position, when the O-ring 2 is arranged at the treating-stage ring angle with respect to the base and the running gantry 3 is arranged at the gantry angle with respect to the O-ring 2. That is, the patient position and the ring-angle offset value are calculated such that the treating-stage orientation coincides with the planning-stage orientation. According to the foregoing patient position, in the radiotherapy apparatus controller 10, when the position of the patient 35 is adjusted, the couch 33 is not required to be rotationally moved around the three rotation axes perpendicular to each other. Consequently, for the radiotherapy apparatus 1, it is possible to apply the two-axes rotation driving device that is more compact than the different couch driving device that can rotate the couch 33 around the three rotation axes. At this time, in the radiotherapy apparatus controller 10, the height of the couch 33 can be made lower, and it is possible to reduce the burden when the patient 35 gets on the couch 33.

In still another embodiment of the radiotherapy apparatus controller according to the present invention, the position-adjusting-stage position data collecting section 63 in the above-mentioned embodiment is replaced with a different position-adjusting-stage position data collecting section. The position-adjusting-stage position data collecting section further controls the gantry driving device so that the running gantry 3 is rotated at a constant angular speed around the gantry rotation axis 12 with respect to the O-ring 2 when the O-ring 2 is arranged at a proper position. The position-adjusting-stage position data collecting section further controls the first diagnostic radiation irradiating device 25 so that the first diagnostic radiation 31 is emitted when the running gantry 3 is arranged at a predetermined gantry angle. As the predetermined gantry angle, an arithmetic progression is exemplified in which a tolerance is 0.5 degrees and a difference between the first term and the final term is 180 degrees. The position-adjusting-stage position data collecting section further controls the first image taking device 27 so that a reconfiguration perspective image is taken when the running gantry 3 is arranged at the predetermined gantry angle with respect to the O-ring 2.

The position-adjusting-stage position data collecting section reconfigures the 3-dimensional data based on a plurality of reconfiguration perspective images. In the 3-dimensional data, a plurality of CT values is correlated to a plurality of voxels. The plurality of voxels corresponds to a plurality of regions, respectively, a space where the patient 35 is arranged being filled with the plurality of regions without any gap.

For example, each of the plurality of regions is formed as a cuboid. One CT value corresponding to an arbitrary voxel among the plurality of CT values corresponds to a transmission coefficient (X-ray absorption coefficient) of a region corresponding to the arbitrary voxel in the plurality of regions. The position-adjusting-stage position data collecting section calculates the position-adjusting-stage position indicating a position and an orientation where the patient 35 is arranged when the plurality of reconfiguration perspective images is taken, based on the 3-dimensional data.

Also, in the radiotherapy apparatus controller to which the foregoing position-adjusting-stage position data collecting section is applied, it is possible to reduce the burden of the patient 35 and reduce a feeling of discomfort of the patient 35, similarly to the radiotherapy apparatus controller 10 in the above-mentioned embodiment.

Incidentally, in the position-adjusting-stage position data collecting section, it is also possible to calculate the position-adjusting-stage position based on values measured by another sensor that differs from the imager system in the radiotherapy apparatus 1. As the sensor, PET (Positron Emission Tomography), MRI (Magnetic Resonance Imaging), and a laser scanner for measuring a 3-dimensional geometric model of a subject are exemplified. Also, in the radiotherapy apparatus controller to which the foregoing position-adjusting-stage position data collecting section is applied, it is possible to reduce the burden of the patient 35 and reduce a feeling of discomfort of the patient 35, similarly to the radiotherapy apparatus controller 10 in the above-mentioned embodiment.

Incidentally, this application claims the benefit of priority based on Japanese Patent Application No. 2010-217356 filed on Sep. 28, 2010, the disclosure of which is incorporated herein in its entirety by reference.

The invention claimed is:

1. A radiotherapy apparatus controller comprising:

a planning-stage position data collecting section configured to collect planning-stage position data which indicates a planning-stage position where a subject is arranged during a planning stage;

a position-adjusting-stage position data collecting section configured to measure position-adjusting-stage 3-dimensional data which indicates a position-adjusting-stage position where the subject is arranged during a position-adjusting stage different from the planning stage;

a correction amount calculating section configured to calculate a treatment-stage position, a gantry-angle offset value and a ring-angle offset value based on the planning-stage position data and the position-adjusting-stage 3-dimensional data;

a treatment plan collecting section configured to collect an irradiation direction in which an irradiation head is arranged with respect to the planning-stage position, the irradiation head being supported by a gantry, the gantry being supported rotatably with respect to a ring, and the ring being supported rotatably with respect to a ring base;

an irradiation head driving section configured to control an irradiation head driving device, which moves the ring and the gantry, based on the irradiation direction such that the ring is arranged at a corrected ring angle with respect to the ring base and the gantry is arranged at a corrected gantry angle with respect to the ring;

a couch configured to rotatably move around a rotational axis parallel to a direction that is fixed with respect to the ring base and move in a parallel direction with respect to the ring base; and a couch driving section that controls a couch driving device which is configured to move the subject from the position-adjusting-stage position to the treatment-stage position, wherein the irradiation direction indicates a gantry angle and a ring angle, wherein the corrected ring angle indicates the difference that the ring-angle offset value is subtracted from the ring angle, wherein the corrected gantry angle indicates the difference that the gantry-angle offset value is subtracted from the gantry angle, wherein the gantry-angle offset value and the ring-angle offset value are calculated such that the irradiation head is arranged in the irradiation direction with respect to the treatment-stage position when the ring is arranged at the corrected ring angle with respect to the ring base and the gantry is arranged at the corrected gantry angle with respect to the ring, wherein a movement of the subject from the position-adjusting-stage position to the treatment-stage position is comprised of the rotational movement around the rotational axis and the parallel movement with respect to the ring base.

2. The radiotherapy apparatus controller according to claim 1, further comprising:

an irradiating section configured to control the irradiation head such that the irradiation head irradiates the subject with a therapeutic radiation after the subject is arranged at the treatment-stage position, the ring is arranged at the corrected ring angle with respect to the ring base and the gantry is arranged at the corrected gantry angle with respect to the ring.

3. The radiotherapy apparatus controller according to claim 1, wherein the couch driving device includes:

a first frame configured to be supported parallel-movably with respect to the ring base;

a second frame supported by the first frame and configured to be supported rotatably around a first rotation axis with respect to the first frame;

a rotational movement driving device configured to move a guide in parallel to a first direction with respect to the first frame;

a slider configured to be supported by the guide movably in parallel to a second direction different from the first direction; and a parallel movement driving device configured to move the second frame in parallel with respect to the ring base, wherein the slider is supported by the second frame rotatably around a second rotation axis different from the first rotation axis.

4. The radiotherapy apparatus controller according to claim 3, wherein the position-adjusting-stage 3-dimensional data indicates a perspective image taken by an imager system supported by the gantry.

5. The radiotherapy apparatus controller according to claim 4, wherein the planning-stage position data indicates 3-dimensional data measured by another modality different form the imager system.

6. The radiotherapy apparatus controller according to claim 1, wherein the treatment-stage position calculates such that the corrected ring angle coincides with the ring angle.

7. The radiotherapy apparatus controller according to claim 1, wherein the treatment-stage position calculates such that the corrected gantry angle coincides with the gantry angle.

8. The radiotherapy apparatus controller according to claim 1, wherein the rotational axis is perpendicular to a ring rotational axis.

9. A radiotherapy apparatus control method comprising:

collecting planning-stage position data which indicates a planning-stage position where a subject is arranged during a planning stage;

collecting position-adjusting-stage 3-dimensional data which indicates a position-adjusting-stage position where the subject is arranged during a position-adjusting stage different from the planning stage;

calculating a treatment-stage position, a gantry-angle offset value and a ring-angle offset value based on the planning-stage position data and the position-adjusting-stage 3-dimensional data;

collecting an irradiation direction in which an irradiation head is arranged with respect to the planning-stage position, the irradiation head being supported by a gantry, the gantry being supported rotatably with respect to a ring, and the ring being supported rotatably with respect to the ring base;

moving a couch such that the subject is moved from the position-adjusting-stage position to the treatment-stage position; and moving the ring and the gantry such that the ring is arranged at a corrected ring angle with respect to the ring base and the gantry is arranged at a corrected gantry angle with respect to the ring, wherein the irradiation direction indicates a gantry angle and a ring angle, wherein the corrected ring angle indicates the difference that the ring-angle offset value is subtracted from the ring angle, wherein the corrected gantry angle indicates the difference that the gantry-angle offset value is subtracted from the gantry angle, wherein the gantry-angle offset value and the ring-angle offset value are calculated such that the irradiation head is arranged in the irradiation direction with respect to the treatment-stage position when the ring is arranged at the corrected ring angle with respect to the ring base and the gantry is arranged at the corrected gantry angle with respect to the ring, wherein a movement of the subject from the position-adjusting-stage position to the treatment-stage position is comprised of a rotational movement around a rotational axis parallel to a direction that is fixed with respect to the ring base and a parallel movement with respect to the ring base.

10. The radiotherapy apparatus control method according to claim 9, wherein the position-adjusting-stage 3-dimensional data indicates a perspective image taken by an imager system supported by the gantry.

11. The radiotherapy apparatus control method according to claim 10, wherein the planning-stage position data indicates 3-dimensional data measured by another modality different from the imager system.

12. The radiotherapy apparatus control method according to claim 9, wherein the treatment-stage position calculates such that the corrected ring angle coincides with the ring angle.

13. The radiotherapy apparatus control method according to claim 9, wherein the treatment-stage position calculates such that the corrected gantry angle coincides with the gantry angle.

14. A non-transient computer readable medium containing program instructions for causing a computer to perform the method of: collecting planning-stage position data which indicates a planning-stage position where a subject is arranged during a planning stage;

collecting position-adjusting-stage 3-dimensional data which indicates a position-adjusting-stage position where the subject is arranged during a position-adjusting stage different from the planning stage;

calculating a treatment-stage position, a gantry-angle offset value and a ring-angle offset value based on the planning-stage position data and the position-adjusting-stage 3-dimensional data;

collecting an irradiation direction in which an irradiation head is arranged with respect to the planning-stage position, the irradiation head being supported by a gantry, the gantry being supported rotatably with respect to a ring, and the ring being supported rotatably with respect to a ring base;

moving a couch such that the subject is moved from the position-adjusting-stage position to the treatment-stage position; and moving the ring and the gantry such that the ring is arranged at a corrected ring angle with respect to the ring base and the gantry is arranged at a corrected gantry angle with respect to the ring, wherein the irradiation direction indicates a gantry angle and a ring angle, wherein the corrected ring angle indicates the difference that the ring-angle offset value is subtracted from the ring angle, wherein the corrected gantry angle indicates the difference that the gantry-angle offset value is subtracted from the gantry angle, wherein the gantry-angle offset value and the ring-angle offset value are calculated such that the irradiation head is arranged in the irradiation direction with respect to the treatment-stage position when the ring is arranged at the corrected ring angle with respect to the ring base and the gantry is arranged at the corrected gantry angle with respect to the ring, wherein a movement of the subject from the position-adjusting-stage position to the treatment-stage position is comprised of a rotational movement around a rotational axis parallel to a direction that is fixed with respect to the ring base and a parallel movement with respect to the ring base.

15. The non-transient computer readable medium according to claim 14, wherein the position-adjusting-stage 3-dimensional data indicates a perspective image taken by an imager system supported by the gantry.

16. The non-transient computer readable medium according to claim 15, wherein the planning-stage position data indicates 3-dimensional data measured by another modality different form the imager system.

17. The non-transient computer readable medium according to claim 14, wherein the treatment-stage position calculates such that the corrected ring angle coincides with the ring angle.

18. The non-transient computer readable medium according to claim 14, wherein the treatment-stage position calculates such that the corrected gantry angle coincides with the gantry angle.

* * * * *